(12) United States Patent
Sharawi et al.

(10) Patent No.: US 11,412,952 B2
(45) Date of Patent: Aug. 16, 2022

(54) RADIO FREQUENCY SENSOR ARRAY FOR DETECTING PULMONARY EDEMA AND EMPHYSEMA

(71) Applicant: King Fahd University of Petroleum and Minerals, Dhahran (SA)

(72) Inventors: Mohammad S. Sharawi, Dhahran (SA); Muhammad Tayyab, Dhahran (SA); Atif Shamim, Thuwal (SA); Abdelsalam Al-Sarkhi, Dhahran (SA)

(73) Assignees: King Fahd University of Petroleum and Minerals, Dhahran (SA); King Abdullah University of Science and Technology, Thuwal (SA)

( * ) Notice: Subject to any disclaimer, the term of this patent is extended or adjusted under 35 U.S.C. 154(b) by 485 days.

(21) Appl. No.: 16/707,728

(22) Filed: Dec. 9, 2019

(65) Prior Publication Data

US 2021/0121095 A1    Apr. 29, 2021

Related U.S. Application Data

(60) Provisional application No. 62/926,692, filed on Oct. 28, 2019.

(51) Int. Cl.
*A61N 1/39*    (2006.01)
*A61B 5/08*    (2006.01)
(Continued)

(52) U.S. Cl.
CPC .............. *A61B 5/08* (2013.01); *A61B 5/0024* (2013.01); *A61B 5/05* (2013.01); *A61B 5/4878* (2013.01);
(Continued)

(58) Field of Classification Search
CPC ........... A61B 5/08; A61B 5/0024; A61B 5/05; A61B 5/4878; A61B 2562/046; A61B 2562/164
See application file for complete search history.

(56) References Cited

U.S. PATENT DOCUMENTS 8,725,311 B1    5/2014  Breed
9,549,682 B2    1/2017  Howie et al.
(Continued)

FOREIGN PATENT DOCUMENTS

CA    2770325    *  2/2011    ............... A61B 5/01
EP    2 862 504 B1    6/2016

OTHER PUBLICATIONS

Salman ; A Wearable Real-Time and Non-Invasive Thoracic Cavity Monitoring System ; The Ohio State University 2015 ; 119 Pages.

*Primary Examiner* — Hongmin Fan
(74) *Attorney, Agent, or Firm* — Oblon, McClelland, Maier & Neustadt, L.L.P.

(57) ABSTRACT

A low complexity, low powered, non-invasive, and wearable system for detecting pulmonary edema and emphysema by estimating an average dielectric constant includes a radio frequency (RF) sensor array, which is fabricated along a flexible substrate, a data collection unit, a body area network (BAN), and a post-processing unit. The flexibility of the flexible substrate allows the RF sensor array to worn around the chest region. A plurality of ports of the RF sensor array is used to measure a set of transmission coefficients. The data collection unit accumulates and transfers the set of transmission coefficients to the post-processing unit, wherein the BAN is used during the transfer process. At the post-processing unit, the average dielectric constant is estimated. Since the average dielectric constant can be used as a measure of fluids and air within the lungs, pulmonary (Continued)

edema and emphysema may be detected using the average dielectric constant.

13 Claims, 16 Drawing Sheets

(51) Int. Cl.
    *A61B 5/05*           (2021.01)
    *A61B 5/00*           (2006.01)

(52) U.S. Cl.
    CPC ... *A61B 2562/046* (2013.01); *A61B 2562/164* (2013.01)

(56) References Cited

U.S. PATENT DOCUMENTS

| | | | |
|---|---|---|---|
| 2006/0100666 A1* | 5/2006 | Wilkinson | A61B 5/085 607/1 |
| 2015/0208949 A1 | 6/2015 | Tupin, Jr. et al. | |

\* cited by examiner

RADIO FREQUENCY SENSOR ARRAY FOR DETECTING PULMONARY EDEMA AND EMPHYSEMA

CROSS REFERENCE TO RELATED APPLICATION

The present application claims benefit of priority to U.S. Provisional Application No. 62/926,692 having a filing date of Oct. 28, 2019 which is incorporated here by reference in its entirety.

BACKGROUND

Field of the Invention

The present disclosure relates to a method and system utilizing a radio frequency (RF) sensor array for detecting pulmonary edema and emphysema. The method and system of the present disclosure estimates an average dielectric constant to detect pulmonary edema and emphysema.

Description of the Related Art

Computed tomography (CT), X-ray, and magnetic resonance imaging (MRI) are the most widely used non-invasive imaging methods currently used in the biomedical industry. Even though these methods have significant advantages, such as accuracy, some notable disadvantages can also be identified. For example, in order to use one of these existing methods, a patient needs to visit a medical center. The equipment related cost, lack of mobility due to the heavy machinery, health risk due to high frequency operation, and unsuitability for continuous operation are among some of the other notable disadvantages. Even though other health monitoring sensors exist for respiration rate, heart rate, and skin temperature measurements, these health monitoring sensors are not suitable for lung deep tissue monitoring due to low depth of penetration.

In contrast to CT imaging, which uses linear X-rays, electrical impedance tomography (EIT), which uses electric currents that travel three dimensionally along the path of least resistivity, can also be used for imaging purposes. Ultrasound guided EIT is another imaging method that is used to address non-linear characteristics associated with EIT. In particular, ultrasound guided EIT is proposed to directly reconstruct a geometric configuration of a target-free interface. However, both EIT and ultrasound guided EIT are expensive, complex, involve large machinery, utilize high frequencies during operation, may produce high errors, associated with complex circuitry, and are limited to bed side applications. Other available detection techniques, such as microwave techniques used for breast cancer detection utilize a high frequency during operation. Moreover, the depth of penetration is low and may not be suitable for continuous monitoring.

In order to address the issues related to the use of high frequencies, RF sensors that operate using low frequencies have been used for detection of lung-related medical conditions. However, since most of the existing RF sensors have a planar geometry, the RF sensors can only monitor the permittivity of a small area and may have a high error value. As a result of the planar geometry, multiple RF sensors need to be linked together and complex post processing techniques need to be performed when being used on a human chest.

In view of the difficulties and drawbacks of the existing detection methods and imaging methods, an objective of the system and method of the present disclosure is to describe a wearable health monitoring sensor that is inexpensive, smaller in size compared to existing detection methods, low in complexity, non-invasive, and utilizes a low amount of power.

SUMMARY OF THE INVENTION

The system and method described in the present disclosure is used to detect pulmonary edema and emphysema by utilizing a radio frequency (RF) sensor array that is fabricated on a flexible substrate. The flexibility of the polyimide substrate allows the RF sensor array to be positioned around the chest of a human. Preferably, the RF sensor array operates at a frequency within a range of 50 Megahertz (MHz)-75 MHz. The flexibility of the polyimide substrate and the power requirements of the RF sensor array, allows the system of the present disclosure to be utilized as a low complexity, low power, small sized, wearable monitoring device. When in use, a plurality of ports of the RF sensor array measures a set of transmission coefficients. The transmission coefficients for each of the plurality of ports is transferred to a post-processing unit via a body area network. The post-processing unit proceeds to estimate an average dielectric constant. The average dielectric constant is used to determine the presence of water/air in human and porcine lungs, which can then be used to detect pulmonary edema and emphysema.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

All illustrations of the drawings are for the purpose of describing selected embodiments of the present disclosure and are not intended to limit the scope of the present disclosure or accompanying claims.

The present disclosure describes a low complexity, low power, small-size, wearable, cost effective, and non-invasive radio frequency (RF) based sensor array for monitoring pulmonary edema and emphysema. The system and method of the present disclosure may be used to detect pulmonary edema and emphysema in a patient, e.g., in a human lung or a porcine lung.

Figure 1:
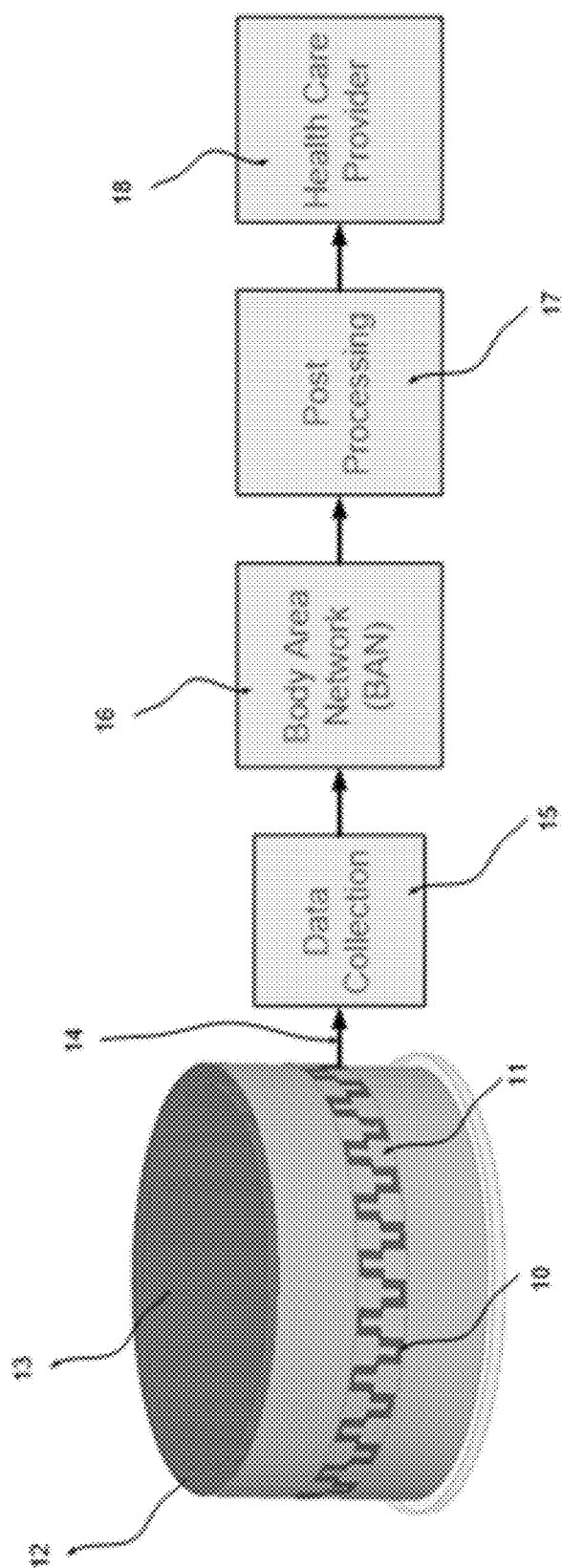
FIG. 1 is a diagram illustrating a system of the present disclosure used for detecting pulmonary edema and emphysema.

As seen in FIG. 1, the system for detecting pulmonary edema and emphysema comprises a radio frequency (RF) sensor array, a data collection unit, a body area network (BAN), and a post-processing unit. The RF sensor array measures a set of transmission coefficients from a human or porcine lung that can be used to estimate an average dielectric constant at the post-processing unit. To do so, the post-processing unit includes circuitry with instructions configured to estimate the average dielectric constant. The average dielectric constant provides information regarding the presence of water/air in the lungs. Therefore, pulmonary edema, which is a condition caused by excess fluid in the lungs, and emphysema, which is a condition where large air spaces are created in the lungs, can be detected using the average dielectric constant. The data collection unit and the BAN are used transfer the set of transmission coefficients to the post-processing unit.

Figure 3:
FIG. 3 is a photograph of the RF sensor array, which is fabricated on the flexible substrate, being positioned around a human torso.

For the system of the present disclosure to be worn around a human torso, which in general has an elliptical shape, the RF sensor array is fabricated along a flexible substrate. As seen in FIG. 3, when in use, the flexible substrate is positioned around a human torso such that the RF sensor array can measure the set of transmission coefficients required for detecting pulmonary edema and emphysema. A transmission coefficient is a measure of how much of an electromagnetic wave (light) passes through a surface or an optical element. In particular, the transmission coefficient describes the amplitude, intensity, or total power of a transmitted wave relative to an incident wave. To be used for detecting pulmonary edema and emphysema, a signal is transmitted through the thorax by positioning the flexible substrate around the human torso.

In a preferred embodiment, an operating frequency of the RF sensor array is within a range of 45 Megahertz (MHz)-80 MHz, 50 MHz-75 MHz, with a preferable frequency of 60 MHz. An input power of the RF sensor is within a range of 0.5 milliwatts (mW)-2 mW, 0.5 mW-1.5 mW, with a preferable input power of 1 mW. With the operating frequency of 60 MHz, a depth of measurement for the RF sensor array is within a range of 9 centimeters (cm)-12 cm, 9 cm-11 cm, with a preferable depth of measurement within a range of 10 cm-12 cm. The RF sensor array utilizes a plurality of electrodes and a plurality of ports in the process of measuring the set of transmission coefficients. If a n number of electrodes is used, a n−1 number of ports is preferably used.

Figure 2:
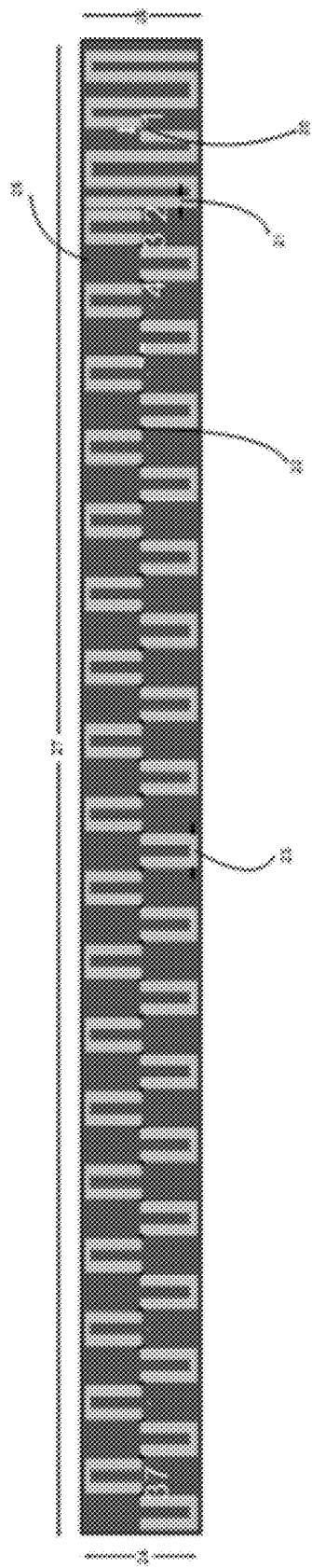
FIG. 2 is a diagram illustrating the geometry and dimensions of a RF sensor array fabricated on a flexible substrate.

In a preferred embodiment, the number of electrodes and the number of ports will be within a range of 30-40 and 35-40. As seen in FIG. 2, preferably, the RF sensor array comprises 38 electrodes and 37 ports. Of the 37 ports, a terminal port is an active port, which is excited with the 60 MHz frequency, and the remainder of the ports are passive ports. Therefore, if the first port is the active port, ports 2-37 will be passive ports. When a preferred embodiment of the system of the present disclosure is used for experimental purposes, a set of coaxial probes with an impedance within the range 45 Ohms-60 Ohms is attached to passive ports. In a preferred embodiment, a distance between two consecutive ports of the plurality of ports is within a range of 0.2 cm-0.3 cm, 0.20 cm-0.25 cm with a preferable distance of 0.22 cm. An exciting electrode of the plurality of electrodes has a width within a range of 0.5 cm-0.8 cm, 0.5 cm-0.7 cm, and 0.5 cm-0.6 cm with a preferable width of 0.57 cm. A set of remaining electrodes will each have a width within a range of 1 cm-4 cm, 2 cm-4 cm, and 1 cm-3 cm with a preferable width of 2 cm. A length of each of the plurality of electrodes is within a range of 3 cm-8 cm, 3 cm-7 cm, 3 cm-5 cm, with a preferable length of 4 cm.

The RF sensor type used in the RF sensor array may be diode detector based or heat based. Diode detector type sensors are generally used for analog power meters. However, the diode detector based may also be used for high performance power meters. The ability to measure signals of extremely low levels of power and respond promptly are some of the advantages of diode detector type sensors. Heat based RF sensors are generally used to dissipate power from a source in a load and measure the resulting temperature rise. Heat based RF sensors can be further classified as thermistors and thermocouple power sensors.

Thermistors provide a method of enabling high quality RF power measurements. Moreover, thermistors enable direct current (DC) power to be substituted to enable a calibration process of a system. The thermistor RF power sensor uses the fact that a temperature rise results from a dissipation of the RF in an RF load.

Thermocouple RF power sensors are widely used in RF and microwave power sensors. Thermocouple RF power sensors exhibit a higher level of sensitivity than thermistor RF power sensors and therefore can be used to detect lower power levels. For example, thermocouple RF power sensors can be used to measure power values in a microwatt range. Furthermore, thermocouple RF and microwave sensors possess a square-law detection characteristic, wherein a produced output is proportional to a square of an input. As a result, the input RF power is proportional to a DC output voltage from the thermocouple sensor.

As described earlier, the RF sensor array is fabricated along and on the flexible substrate. In a preferred embodiment, the fabrication process is completed via inkjet printing, and silver ink is preferably used for printing. In a preferably embodiment, the RF sensor array is printed on both the front and back sides of the flexible substrate. As a first step of the fabrication process, the flexible substrate is washed with isopropyl alcohol (IPA). In a second step, the flexible substrate is dried, e.g., using nitrogen gas. Next, silver ink is printed on the flexible substrate and ultra-violet (UV) light curing is performed on the flexible substrate which is a flexible polyimide sheet in a preferred embodiment. Preferably, the UV light curing process is performed for approximately 1 minute when silver ink is used for printing as in a preferred embodiment. With an increase in curing time, the spread of the silver ink will also increase. In a fourth step, the flexible substrate is fixed on the inkjet printer. In a preferred embodiment, three silver ink layers are printed on the flexible substrate to achieve the required conductivity values. In doing so, after each layer of printing, 10 minutes of heating is applied at a temperature of 130 Centigrade (° C.). After the third layer of printing, the heating time is increased to 15 minutes. In a preferred embodiment, the drop spacing, which is the spot size a printing fluid on a substrate, is selected to be within a range of 25 micrometers (μm)-40 μm, 25 μm-35 μm with a preferable drop spacing of 30 μm.

Even though inkjet printing is utilized in a preferred embodiment of the present disclosure, techniques such as screen printing, aerosol jet printing, evaporation printing, micro contact printing, and nano-imprint lithography may be used in other embodiments of the present disclosure.

Screen printing is a printing technique where a mesh is used to transfer ink onto a substrate, except in areas made impermeable to the ink by a blocking stencil. A blade or squeegee is moved across a screen to fill the open mesh apertures with ink, and a reverse stroke then causes the screen to touch the substrate momentarily along a line of contact. The contact causes the ink to wet the substrate and be pulled out of the mesh apertures as the screen springs back after the blade has passed. When used for electronic printing, aluminum paste is dispensed over the whole surface of the back for passivation and surface reflection. One of the parameters that can vary and can be controlled in screen printing is the thickness of the print. Thus, screen printing is widely used in printing solar cells, electronics etc. In particular, screen printing is appropriate for fabricating electrics and electronics due to its ability to produce patterned, thick layers from paste-like materials. Screen printing can produce conducting lines from inorganic materials (e.g. for circuit boards and antennas), but also insulating and passivating layers, whereby layer thickness is more important than high resolution. In addition to being used for conductive and dielectric layers, screen printing can also be used for printing organic semiconductors.

In aerosol jet printing, the aerosol jet process begins with the atomization of an ink via ultrasonic or pneumatic means, producing droplets on the order of one to two micrometers in diameter. The droplets then flow through a virtual impactor which deflects the droplets having lower momentum away from the stream such that a tight droplet size distribution can be maintained. The droplets are entrained in a gas stream and delivered to the print head. At this step, an annular flow of clean gas is introduced around the aerosol stream to focus the droplets into a tightly collimated beam of material. The combined gas streams exit the print head through a converging nozzle that compresses the aerosol stream to a diameter as small as 10 μm. The jet of droplets exits the print head at high velocity (~50 meters/second) and impinges upon the substrate.

Evaporation printing uses a combination of high precision screen printing with material vaporization to print features in a micrometer range. The evaporation printing method uses techniques such as thermal, e-beam, sputter and other traditional production technologies to deposit materials through a high precision shadow mask (or stencil) that is registered to the substrate. By layering different mask designs and/or adjusting materials, reliable, cost-effective circuits can be built additively, without the use of photolithography, which is a process used in microfabrication to pattern parts of a thin film or the bulk of a substrate.

Micro contact printing (or μCP) is a form of soft lithography that uses the relief patterns on a master polydimethylsiloxane (PDMS) stamp to form patterns of self-assembled monolayers (SAMs) of ink on the surface of a substrate through conformal contact as in the case of nano-transfer printing (nTP). The applications of micro contact printing are wide-ranging including microelectronics, surface chemistry and cell biology.

Nanoimprint lithography (NIL) is a method of fabricating nanometer scale patterns. In particular, NIL is a simple nanolithography process with low cost, high throughput and high resolution that creates patterns by mechanical deformation of imprint resist and subsequent processes. The imprint resist is typically a monomer or polymer formulation that is cured by heat or UV light during the imprinting. Adhesion between the imprint resist and the template is controlled to allow proper release.

In a preferred embodiment, a thickness of the flexible substrate is within a range of 25 micrometers (μm)-75 μm, with a preferable thickness of 50 μm. When the system of the present disclosure is in use, the flexible substrate is in contact with a chest of a human. The flexible substrate is designed to be positioned around a chest that has a radius within a range of 10 cm-15 cm. To do so, the overall length of the flexible substrate can be within a range of 80 cm-100 cm, 80 cm-95 cm, or 85 cm-95 cm, with a preferable length of approximately 90 cm. Moreover, a width of the flexible substrate is within a range of 3.5 cm-5.5 cm, 4.0 cm-5.5 cm, or 4.0-5.0 cm, with a preferable width of approximately 4.5 cm.

In a preferred embodiment, the flexible substrate is a flexible polyimide sheet. In general, polyimides exhibit an exceptional combination of thermal stability (>500 Centigrade), mechanical toughness, and chemical resistance. Additionally, when considering the dielectric properties, polyimides generally have a dielectric constant within a range of 3.0-3.6 with a preferable range of 3.1-3.55, a dielectric strength within a range of 20.0 kilovolts per millimeter (kV/mm)-28.0 kV/mm with a preferable range of 22.0 kV/mm-27.6 kV/mm, a dissipation factor within a range of 0.0015-0.0052 with a preferable range of 0.0018-0.0050, and a volume resistivity within a range of $12\times10^{15}$-$20\times10^{15}$ Ohm centimeter (Ωcm) with a preferable range of $14\times10^{15}$ Ωcm-$18\times10^{15}$ Ωcm. Even though polyimide is used as the flexible substrate in a preferred embodiment, polyether ether ketone (PEEK), transparent conductive polyester, or fluorene polyester may also be used in other embodiments of the present disclosure.

As described earlier, the data collection unit and the BAN are used to transfer the set of transmission coefficients to the post-processing unit. To do so, the RF sensor array is communicably coupled with the data collection unit through a microcontroller and a RF switch. When the RF switch is on, the microcontroller transfers the set of transmission coefficients to the data collection unit. The data collection unit is preferably a portable computing device that can be, but is not limited to, a mobile phone, a computer, and a tablet. The data collection unit is communicably coupled with the post-processing unit through the BAN allowing the BAN to transfer the set of transmission coefficients to the post-processing unit. When the set of transmission coefficients is received at the post-processing unit, the post-processing unit proceeds to estimate an average dielectric constant from the set of transmission coefficients. The average dielectric constant, which provides information regarding the dielectric properties of the lungs, can be transferred onto a health care provider such that pulmonary edema or emphysema may be detected.

The body area network preferably satisfies Institute of Electrical and Electronics Engineers (IEEE) standards IEEE 802.15.4J, IEEE 802.15.6, and other standards within the IEEE 802 family of IEEE standards dealing with local area networks and metropolitan area networks. The BAN is a short range wireless network comprising of devices positioned in, on, and around the body. Three different types of data transmission techniques may be used in BAN implementations: electric-field communication, electric-current communication, and electromagnetic (radio-wave) communication.

Electric-field communication is driven by electric induction, wherein the non-contact approach relies on changes in the electric charge on the surface of the body. Electric-current communication utilizes a trace of currents that pass through the body of the user the BAN is implemented on. The method requires the user to make contact with the electrodes in order to send or receive data. In electromagnetic communication, data transmissions are generally carried out at high frequencies, either in the UHF band (from 300 megahertz (MHz) to 3 gigahertz (GHz)) or in the ultra-wide band (3.1 GHz to 10.6 GHz).

In a method of utilizing the system of the present disclosure, an average dielectric constant is estimated to detect pulmonary edema and emphysema. Since pulmonary edema is a condition caused by excess fluid in the lungs, and emphysema is a condition in which large air spaces are created within the lungs, by estimating the average dielectric constant, which is reflective of the presence of water/air in human lungs or porcine lungs, pulmonary edema and emphysema may be detected.

The average dielectric constant can be expressed as a sum of products of a weight coefficient and a transmission coefficient of each port of the plurality of ports of the RF sensor array of the present disclosure. Thus, the average dielectric constant can be represented as shown in equation 1.

$$\varepsilon_r = \Sigma_{i=2}^{37} w_{i-1} S_{i1} \qquad (1)$$

Figure 4:
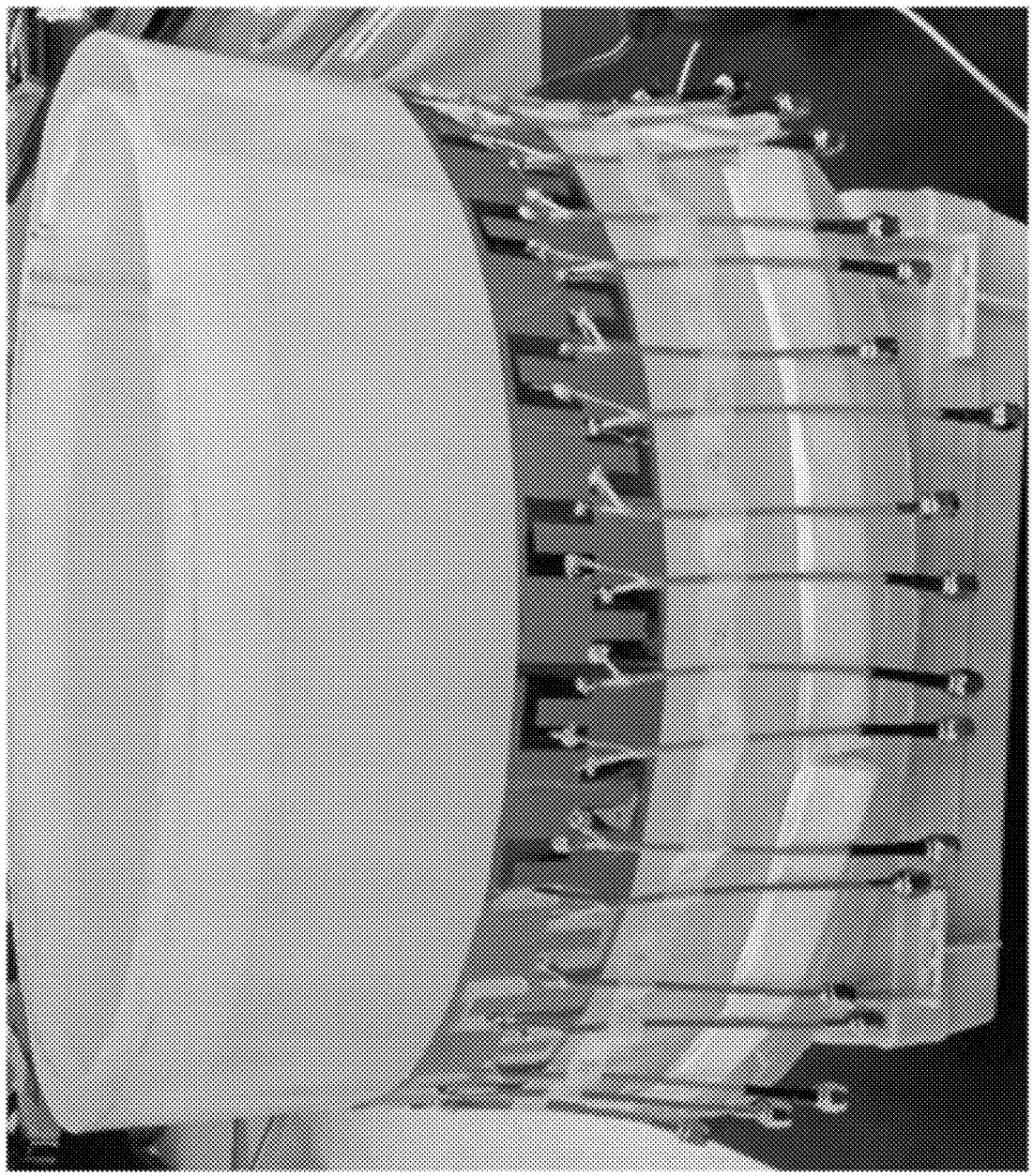
FIG. 4 is a photograph of the RF sensor array fabricated on the flexible substrate being perimetrically positioned around a human chest model.

Where:
$\varepsilon_r$—dielectric constant;
w—weight coefficient;
S—transmission coefficient;
i—port number selected from the plurality of ports;

In order to determine the average dielectric constant, and then use the average dielectric constant to detect pulmonary edema and emphysema, the system of the present disclosure is preferably calibrated. As an initial step of calibrating the RF sensor array, a simulated set of transmission coefficients is determined for the plurality of ports. In a preferred embodiment, a high frequency structure simulator (HFSS) module is used for determining the simulated set of transmission coefficients. HFSS is one of several commercial tools used for antenna design, and the design of complex radio frequency electronic circuit elements including filters, transmission lines, and packaging. HFSS is a commercial finite element method solver for electromagnetic structures, wherein a finite element method is a numerical method for solving problems of engineering and mathematical physics. Typical problem areas of interest include structural analysis, heat transfer, fluid flow, mass transport, and electromagnetic potential. As seen in FIG. 4, for calibration purposes, the RF sensor array is perimetrically positioned around a human chest model that is representative of a human chest.

In a preferred embodiment, the human chest model is created using a computer numerical control (CNC) machine. A Plexiglass sheet with a thickness within a range of 0.5 cm-2 cm, 0.5 cm-1.5 cm, with a preferable thickness of 1 cm is used as a base for the human chest model. Two elliptical grooves for an outer and inner layer of the human chest model are created with a 0.5 cm thickness to attach the flexible 0.8 mm FR-4 sheets, wherein FR-4 sheets are composite material composed of woven fiberglass. The FR-4 sheets are used to separate the inner and outer layer solutions from one another. The height of the human chest model is within a range of 15 cm-20 cm, with a preferable height of approximately 18.29 cm. The FR-4 sheets are attached with adhesive.

Figure 5:
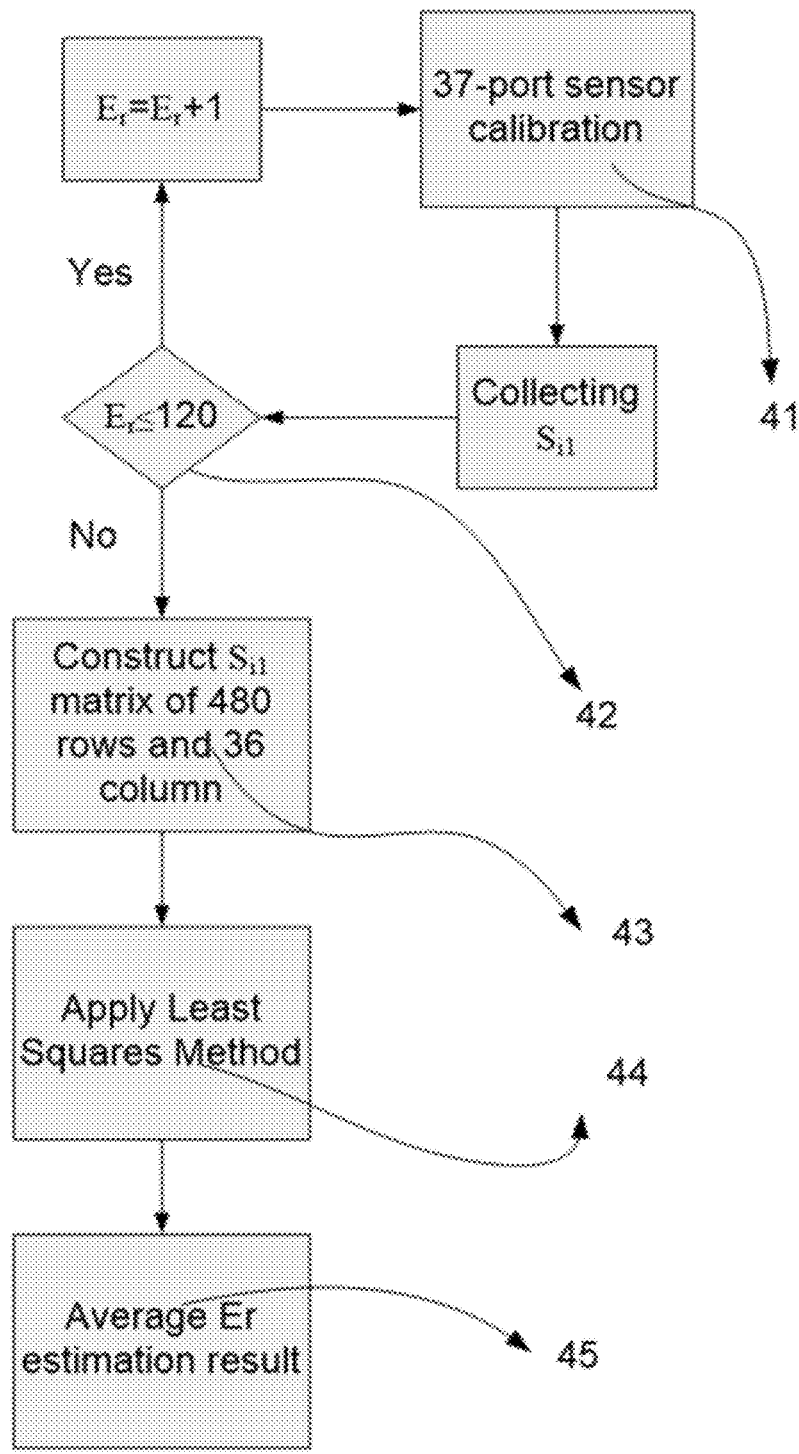
FIG. 5 a flowchart illustrating a basic overall process of calibrating the RF sensor array of the present disclosure to be used for estimating the average dielectric constant.

Each transmission coefficient of the simulated set of transmission coefficients corresponds to a port of the plurality of ports of the RF sensor array. More specifically, each port of the plurality of ports provides a simulated transmission coefficient. As illustrated in FIG. 5, during calibration, the simulated set of transmission coefficients is determined for a set of varying dielectric constant values, a set of varying conductivity values, and a set of varying loss tangent values of the human chest model. More specifically, the set of varying dielectric constant values is representative of different dielectric constants of a chest. The set of varying conductivity values is representative of different electrical conductivity values of a tissue sample. The set of loss tangent values, wherein the loss tangent value defines a lossy reaction to an electric field, is representative of the loss characteristics of a biological tissue. To simulate the varying dielectric constants, conductivity, and loss tangent values, the conditions applied at the inner layer of the human chest model are varied when the human chest model is used.

Preferably, a dielectric assessment kit (DAK) is used to measure the set of varying dielectric constants, the set of varying conductivity values, and the set of varying loss tangent values at the inner layer. In a preferred embodiment, the dielectric constant of the inner layer is varied from 1 to 120. Moreover, the conductivity value of the inner layer is varied from 0.3 siemens/meter (S/m)-0.5 s/m, and the loss tangent value of the inner layer is varied from 3 to 5.

In a preferred embodiment, the electrical properties, namely the dielectric constants, the conductivity values, and the loss tangent values, are applied at the inner layer using a mixture of sodium chloride (NaCl), water, isopropyl alcohol (IPA), and glycerin. Within a frequency range of 10 MHz-100 MHz, glycerin has the highest dielectric constant and IPA has the lowest dielectric constant. Due to its low dielectric constant, IPA may be used in the inner layer during the experiments for emphysema cases. Different solutions were developed to represent normal, edema and emphysema infected human lungs. A 10 milliliter (mL) IPA with 80 mL glycerin solution is used for a normal human lung. For the edema infected lung, a mixture of 200 mL glycerin, 40 mL water, and 10 g NaCl is used. Porcine lung properties are formed using a 200 mL water with 0.7 g NaCl solution. The NaCl-water solution was used to increase the permittivity, electric conductivity, and loss tangent values. The human chest model outer layer properties are optimized using 70 mL IPA, 50 mL glycerin, 20 mL water, and 5 g NaCl solution.

When the simulated set of transmission coefficients is determined as described, an overdetermined matrix is generated for the simulated set of transmission coefficients at the post-processing unit. In general, a system of equations is considered to be overdetermined if there are more equations than unknowns. When such a system is in matrix form, the rows of the coefficient matrix outnumber the columns. Accordingly, in a preferred embodiment, when the set of transmission coefficients is represented in the overdetermined matrix, the overdetermined matrix includes 480 rows and 36 columns.

A method of least squares is applied to the overdetermined matrix to determine a weight coefficient, $w_{i-1}$, for each of the plurality of ports. The method of least squares is a standard approach in regression analysis to approximate the solution of overdetermined systems, wherein the use of least squares minimizes the sum of the squares of the residual made in the results of each equation of the overdetermined system.

When the system of the present disclosure is calibrated as described, and the weight coefficient is determined, the system of the present disclosure may be used to detect pulmonary edema or emphysema of a human or porcine lung. In doing so, the RF sensor array which is fabricated on the flexible substrate is positioned perimetrically around the chest of a human or porcine. After being appropriately positioned around the chest, a measured set of transmission coefficients is determined using the RF sensor array. Next, the RF switch is activated such that the microcontroller can transfer the measured set of transmission coefficients to the data collection unit, wherein the measured set of transmission coefficients is accumulated at the data collection unit. In order to estimate an average dielectric constant, the measured set of transmission coefficients is transferred to the post-processing unit using the BAN. At the post-processing unit, the average dielectric constant is estimated as a sum of products of the weight coefficients of each port and a measured transmission coefficient of each port, wherein the measured set of transmission coefficients includes the measured transmission coefficient.

In a preferred embodiment, to reduce measurement inaccuracies, a vector network analyzer (VNA) is used when determining the measured set of transmission coefficients. The VNA is generally used to test component specifications and verify design simulations to ensure systems and the associated components work accurately. A VNA contains both a source, used to generate a known stimulus signal, and a set of receivers, used to determine changes to this stimulus caused by the device-under-test or DUT. The stimulus signal is injected into the DUT and the VNA measures both the signal that's reflected from the input side, as well as the signal that passes through to the output side of the DUT. The VNA receivers measure the resulting signals and compare them to the known stimulus signal. VNAs perform two types of measurements—transmission and reflection. Transmission measurements pass the VNA stimulus signal through the device under test, which is then measured by the VNA receivers on the other side. The most common transmission S-parameter measurements are S21 and S12 (Sxy for greater than 2-ports). Swept power measurements are a form of transmission measurement. Some other examples of transmission measurements include gain, insertion loss/phase, electrical length/delay and group delay.

In utilizing the VNA, a set of preliminary transmission coefficients is determined for a selected port of the plurality of ports. Preferably, at least three transmission coefficients are recorded as the set of preliminary transmission coefficients. Next, the set of preliminary transmission coefficients is averaged, and the average is determined to be the measured transmission coefficient for the selected port.

Figure 6:
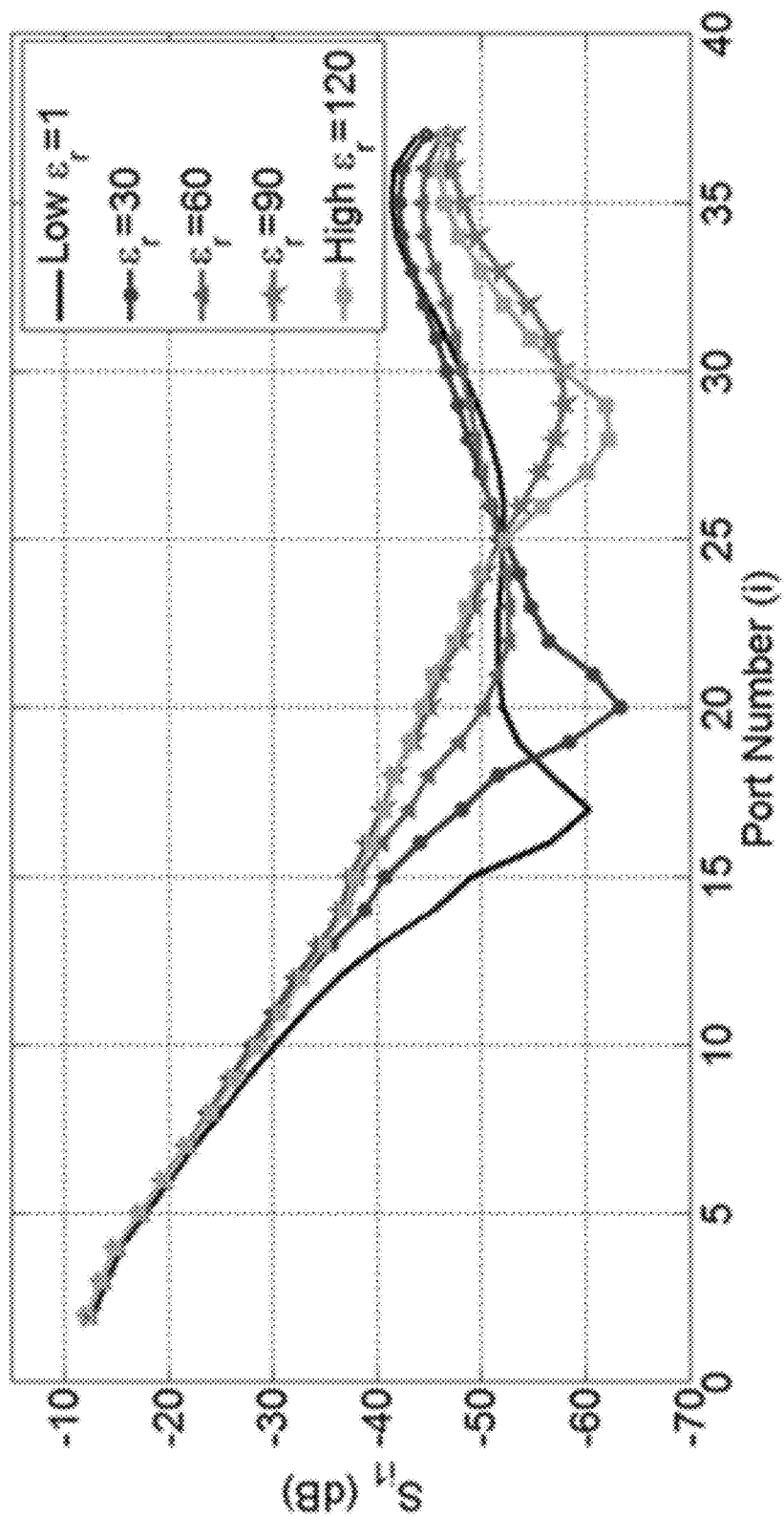
FIG. 6 is a graph illustrating the power levels recorded for different dielectric constants at each of the plurality of ports at different dielectric constant values.

In an experimental setup of a preferred embodiment of the present disclosure, transmission coefficients were obtained for different dielectric constants of the inner layer of the flexible substrate. In particular, the transmission coefficients were measured when the dielectric constant for the inner layer is $\varepsilon_r$=1, 30, 60, 90, and 120. The resulting graph for the transmission coefficients at different dielectric constant values for each of the plurality of ports is shown in FIG. 6. As seen in FIG. 6, a dynamic range of the system has a maximum value of 20 decibel (dB) at port 17, wherein the dynamic range is the range associated with the most affected port by the inner layer dielectric constant values. A wider dynamic range, which has a higher resolution, allows dielectric properties to be mapped accurately with less errors. More specifically, with the wider dynamic range, small changes in $\varepsilon_r$ can be detected more precisely.

Figure 7A:
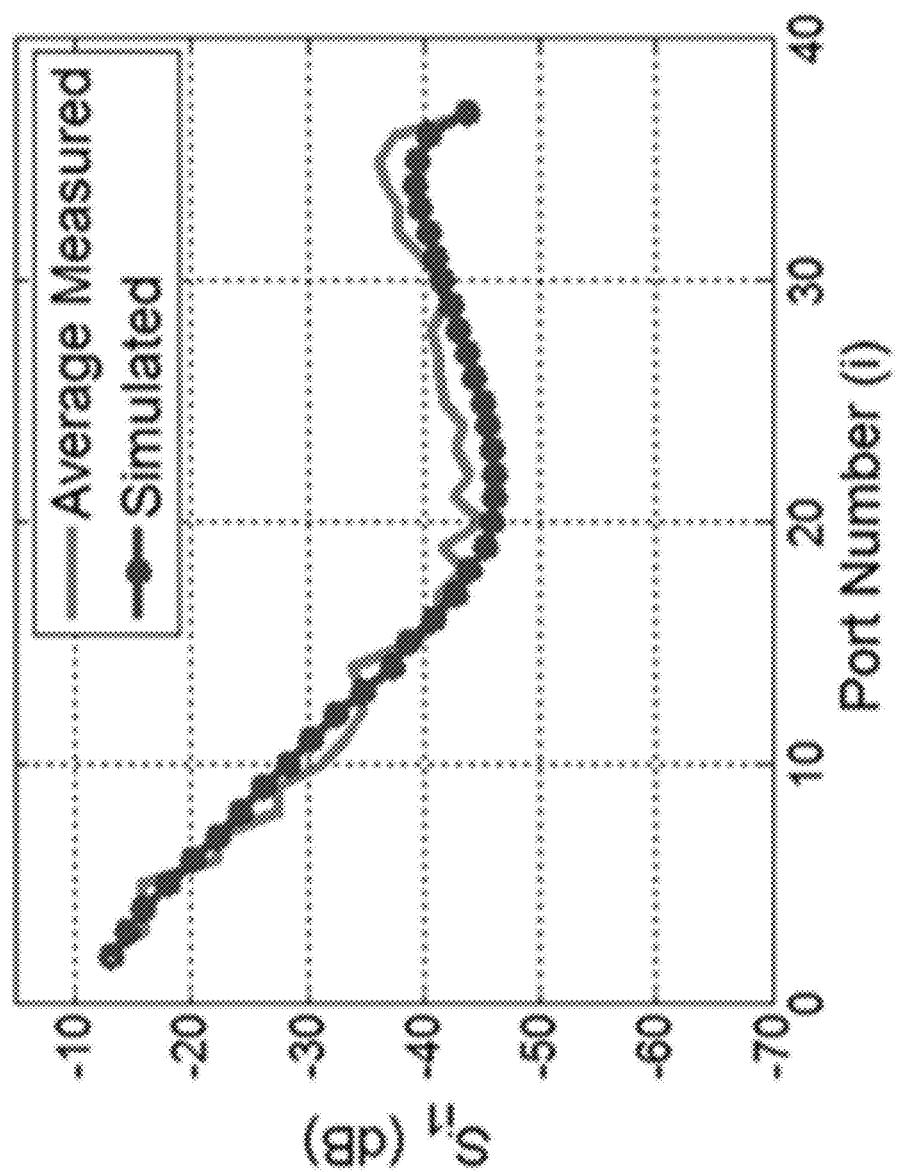
FIG. 7A is a graph comparing an average measured and a simulated transmission coefficient distribution for a normal human lung.
Figure 7B:
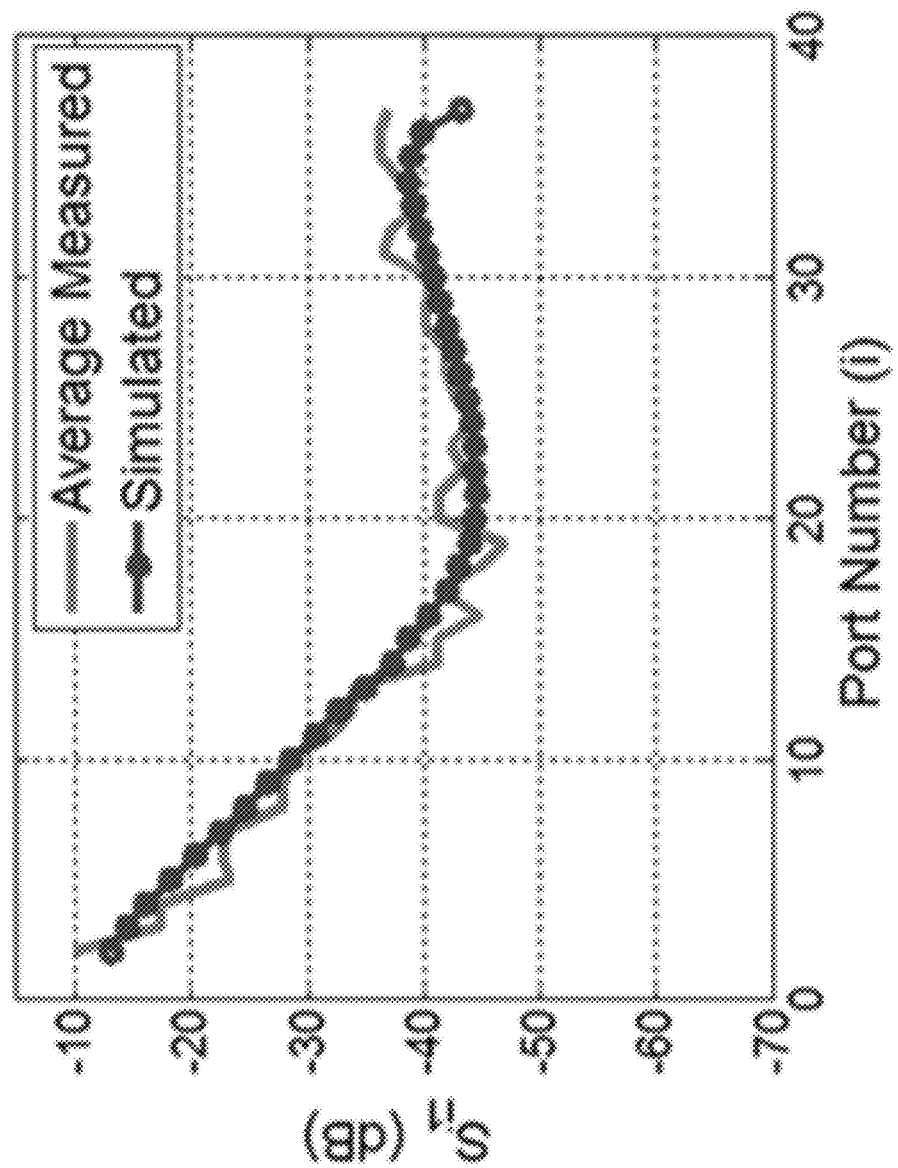
FIG. 7B is a graph comparing an average measured and a simulated transmission coefficient distribution for an emphysema infected human lung.
Figure 7C:
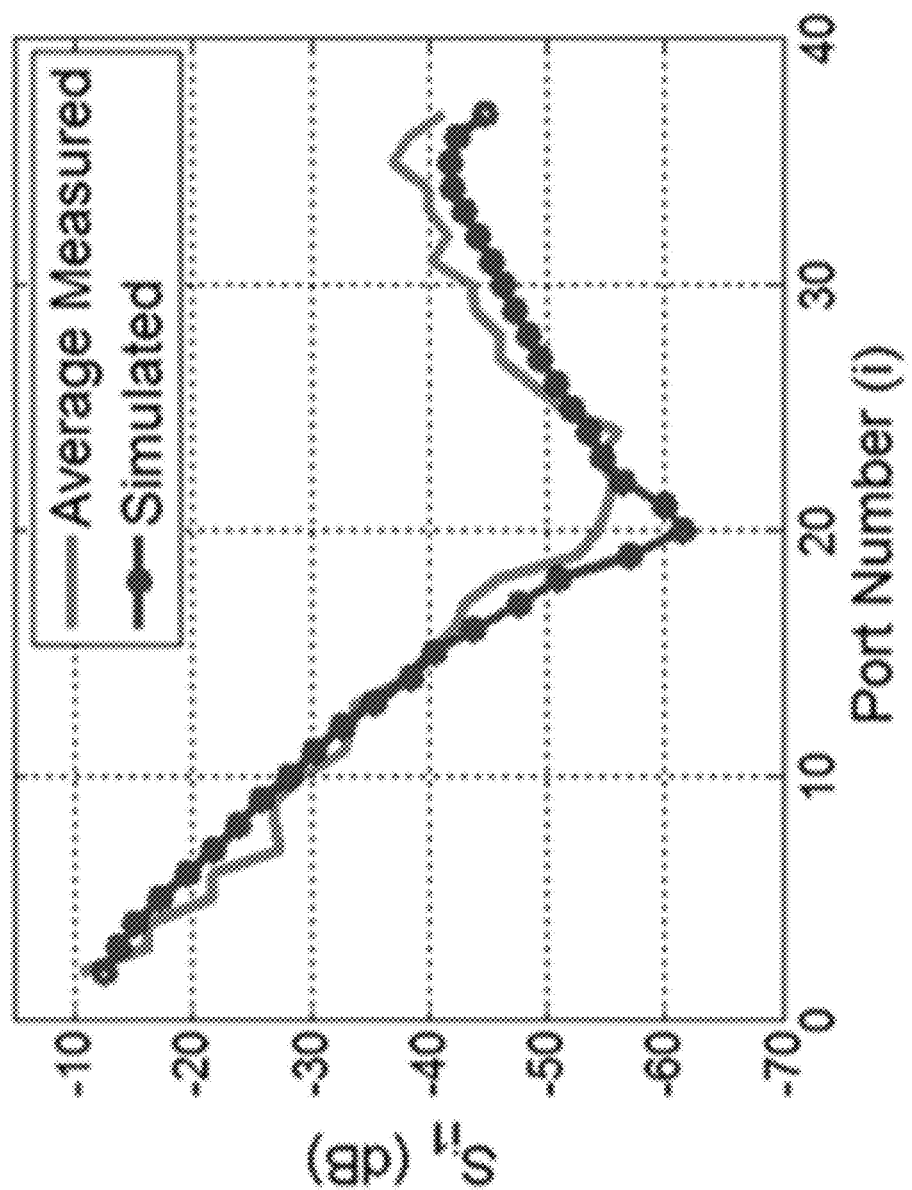
FIG. 7C is a graph comparing an average measured and a simulated transmission coefficient distribution for an edema infected human lung.
Figure 7D:
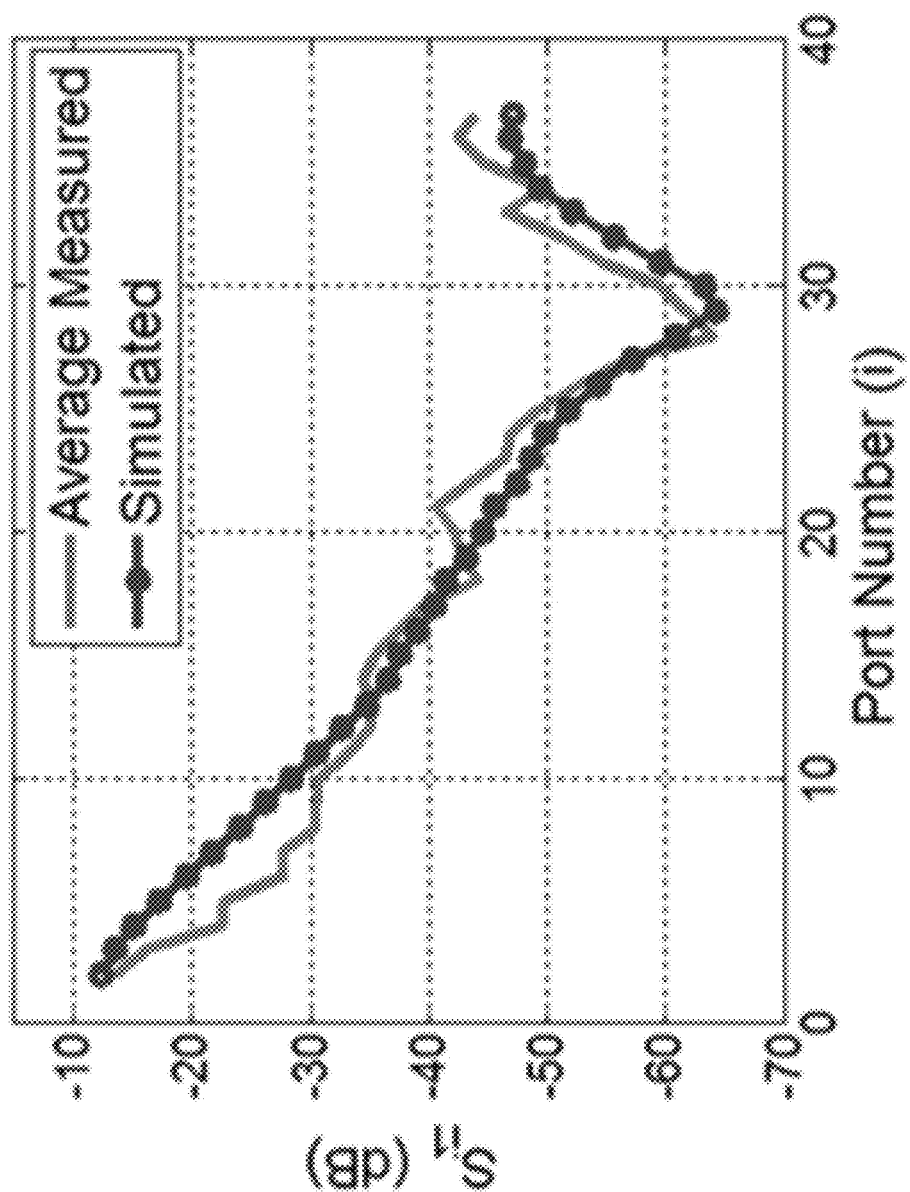
FIG. 7D is a graph comparing an average measured and a simulated transmission coefficient distribution for a normal porcine lung.
Figure 7E:
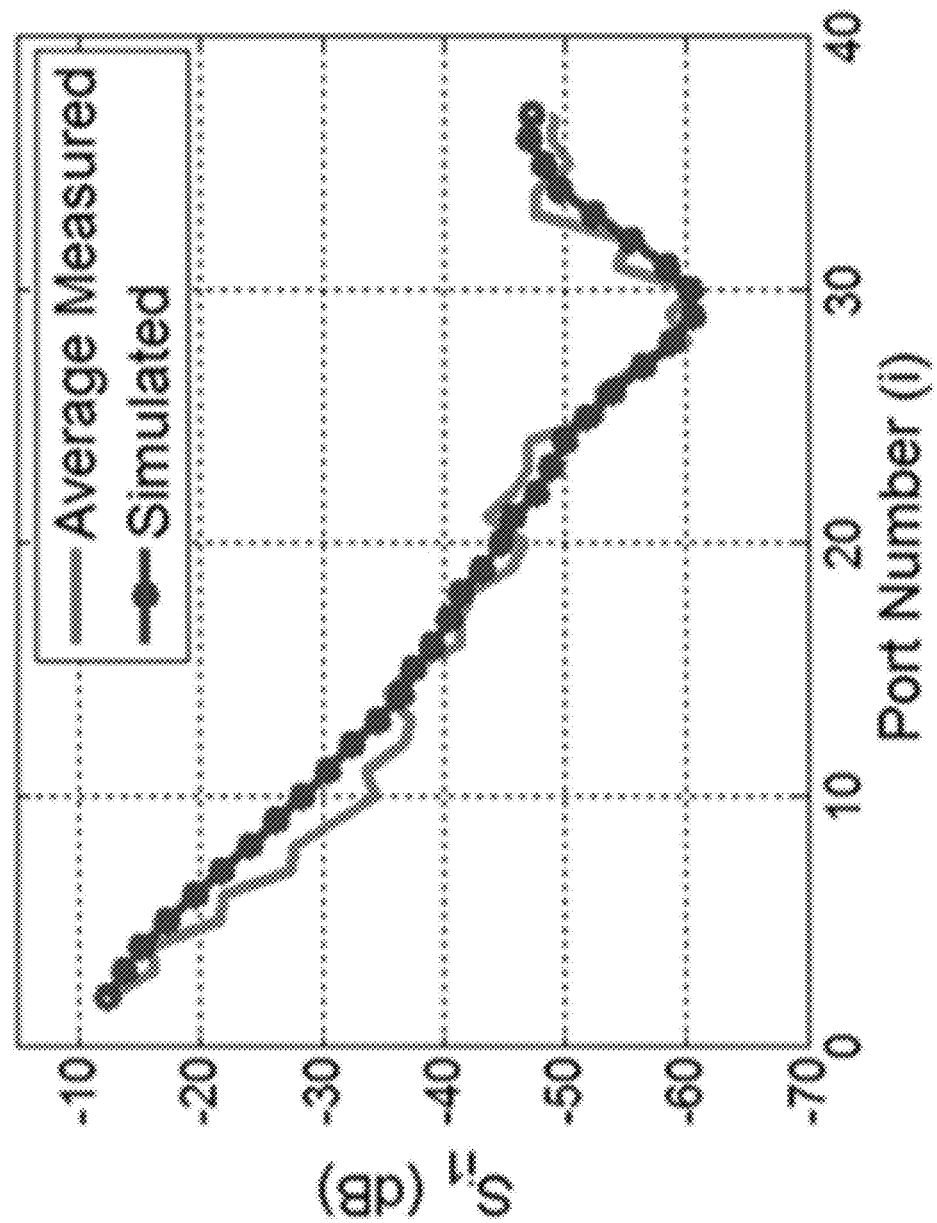
FIG. 7E is a graph comparing an average measured and a simulated transmission coefficient distribution for a porcine lung with first stage of pulmonary edema.
Figure 7F:
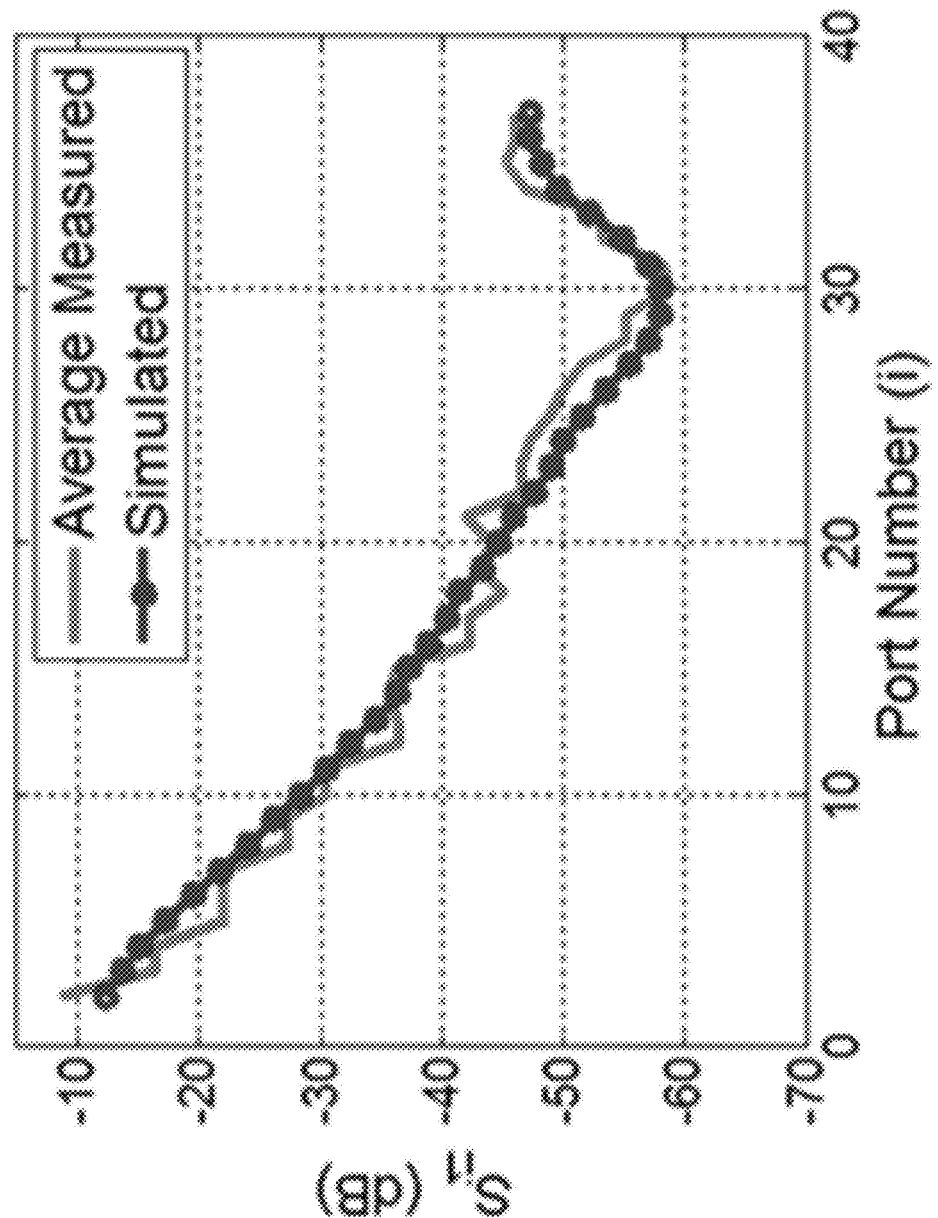
FIG. 7F is a graph comparing an average measured and a simulated transmission coefficient distribution for a porcine lung with second stage of pulmonary edema.

To validate the accuracy of the transmission coefficients measured by the RF sensor array, in FIG. 7A, the distribution of the measured of transmission coefficients is compared against the simulated set of transmission coefficients obtained for a normal human lung. In FIG. 7B, the distribution of the measured set of transmission coefficients is compared against the simulated set of transmission coefficients obtained for a emphysema infected human lung. In FIG. 7C, the distribution of the measured set of transmission coefficients is compared against the simulated set of transmission coefficients obtained for a edema infected human lung. In FIG. 7D, the distribution of the measured set of transmission coefficients is compared against the simulated set of transmission coefficients obtained for a normal porcine lung. In FIG. 7E, the distribution of the measured set of transmission coefficients is compared against the simulated set of transmission coefficients obtained for a porcine lung with first stage of pulmonary edema. In FIG. 7F, the distribution of the measured set of transmission coefficients is compared against the simulated set of transmission coefficients obtained for a porcine lung with second stage of pulmonary edema.

In order to determine an error value of the average dielectric constant determined by the system and method of the present disclosure, the average dielectric constant is compared with a theoretical and numerical value of human and porcine lungs as shown in table 1.

The values of the dielectric constant for the normal lung, emphysema, and edema conditions are 34.2, 16.9, and 51.2, respectively. As described earlier, the outer layer electrical properties are formed using a mixture of isopropyl alcohol, NaCl, water, and glycerin. A mixture of 1190 mL IPA, 850 mL glycerin, 340 mL water, and 85 grams (g) NaCl at the outer layer of the upper chest torso results in a 40.6 dielectric constant. An 8000 mL glycerin and 1000 mL isopropyl alcohol mixture filled the inner layer of the torso with a dielectric constant of 34.2 is similar to a normal lung tissue. A port-A of the VNA is connected to the active port and a port-B of the VNA is switched to the passive ports of the plurality of ports for transmission coefficient measurements. A mixture of 7500 mL glycerin, 1500 mL water, and 375 g NaCl solution filled the inner layer of the chest upper torso results in a dielectric constant of 51.2 which may be used to simulate a lung infected with edema.

Another test was conducted for a porcine lung to show the applicability of the sensor under different conditions. The dielectric constant for the porcine lung is equal to 106.8. The normal water and NaCl solution is applied at the inner layer of the chest upper torso in a ratio of 0.7 g of NaCl in 200 mL of water. Overall, 9000 mL of water and 3.15 g of NaCl is used for this case.

To consider different stages of pulmonary edema and making the chest inner layer more nonhomogeneous, small balloons of 200 mL size were filled with water and inserted to this layer. The effective dielectric constant of water and NaCl mixture including the water balloons is calculated using:

$$\sqrt{\varepsilon_r} = d\sqrt{\varepsilon_{water+salt}} + w\sqrt{\varepsilon_{water}}$$

Where:
d—Volume fraction of water and NaCl solution;
w—volume of water;
$\varepsilon_{water+salt}$—dielectric constant of a water and NaCl solution=108;
$\varepsilon_{water}$—dielectric constant of water=81;

By adding 6 water balls to the inner layer, the obtained average dielectric constant may be altered to be 104. By adding 12 water balls to the inner layer, the obtained average dielectric constant may be altered to be 100. By adding 18 water balls to the inner layer, the obtained average dielectric constant may be altered to be 96.

| Sr. No. | Case | Theoretical $\varepsilon_r$ | Numerical $\varepsilon_r$ | Measured $\varepsilon_r$ | Measured Error (%) |
|---|---|---|---|---|---|
| 1 | Normal Lung | 34.2 | 33.74 | 32.99 | 3.54 |
| 2 | Emphysema infected Lung | 19.5 | 19.47 | 18.72 | 4 |
| 3 | Edema infected Lung | 51.2 | 51.74 | 53.67 | 4.83 |
| 4 | Porcine Lung | 108 | 109.31 | 110.89 | 2.68 |
| 5 | Porcine Lung adding 6 water balls | 104 | 104.83 | 104.9 | 0.87 |
| 6 | Porcine Lung adding 12 water balls | 100 | 100.3 | 102.18 | 2.18 |
| 7 | Porcine Lung adding 18 water balls | 96 | 96.52 | 98.69 | 2.8 |

As seen in table 1, the error value of the average dielectric constant estimated by the system and the method of the present disclosure varies less than 5% of the theoretical and numerical values measured for human lungs, and varies less than 3% of the theoretical and numerical values measured for porcine lungs.

Figure 8:
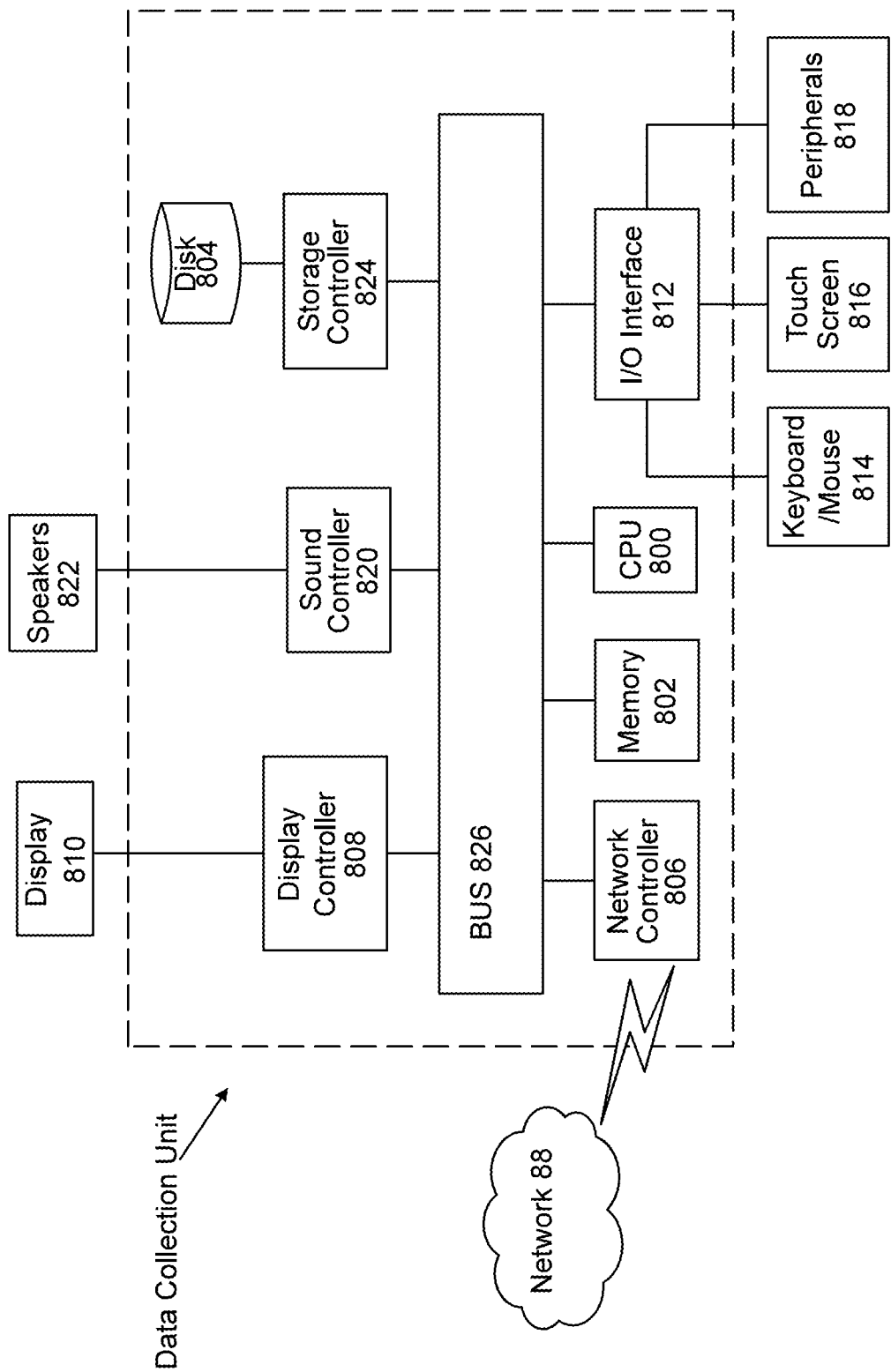
FIG. 8 is a schematic block diagram illustrating a hardware configuration of a data collection unit associated with an average dielectric constant determining process of the method of the present disclosure.

Next, a hardware description of the data collection unit according to exemplary embodiments is described with reference to FIG. 8. In FIG. 8, the data collection unit includes a CPU 800 which performs the processes described above/below. The process data and instructions may be stored in memory 802. These processes and instructions may also be stored on a storage medium disk 804 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the data collection unit communicates, such as a server or computer.

Further, the claimed advancements may be provided as a utility application, background daemon, or component of an operating system, or combination thereof, executing in conjunction with CPU 800 and an operating system such as Microsoft Windows 7, UNIX, Solaris, LINUX, Apple MAC-OS and other systems known to those skilled in the art.

The hardware elements in order to achieve the data collection unit may be realized by various circuitry elements, known to those skilled in the art. For example, CPU 800 may be a Xenon or Core processor from Intel of America or an Opteron processor from AMD of America, or may be other processor types that would be recognized by one of ordinary skill in the art. Alternatively, the CPU 800 may be implemented on an FPGA, ASIC, PLD or using discrete logic circuits, as one of ordinary skill in the art would recognize. Further, CPU 800 may be implemented as multiple processors cooperatively working in parallel to perform the instructions of the inventive processes described above.

The data collection unit in FIG. 8 also includes a network controller 806, such as an Intel Ethernet PRO network interface card from Intel Corporation of America, for interfacing with network 88. As can be appreciated, the network 88 can be a public network, such as the Internet, or a private network such as an LAN or WAN network, or any combination thereof and can also include PSTN or ISDN subnetworks. The network 88 can also be wired, such as an Ethernet network, or can be wireless such as a cellular network including EDGE, 3G and 4G wireless cellular systems. The wireless network can also be WiFi, Bluetooth, or any other wireless form of communication that is known.

The data collection unit further includes a display controller 808, such as a NVIDIA GeForce GTX or Quadro graphics adaptor from NVIDIA Corporation of America for interfacing with display 810, such as a Hewlett Packard HPL2445w LCD monitor. A general purpose I/O interface 812 interfaces with a keyboard and/or mouse 814 as well as a touch screen panel 816 on or separate from display 810. General purpose I/O interface also connects to a variety of peripherals 818 including printers and scanners, such as an OfficeJet or DeskJet from Hewlett Packard.

A sound controller 820 is also provided in the data collection unit, such as Sound Blaster X-Fi Titanium from Creative, to interface with speakers/microphone 822 thereby providing sounds and/or music.

The general purpose storage controller 824 connects the storage medium disk 804 with communication bus 826, which may be an ISA, EISA, VESA, PCI, or similar, for interconnecting all of the components of the data collection unit. A description of the general features and functionality of the display 810, keyboard and/or mouse 814, as well as the display controller 808, storage controller 824, network controller 806, sound controller 820, and general purpose I/O interface 812 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 9.

Figure 9:
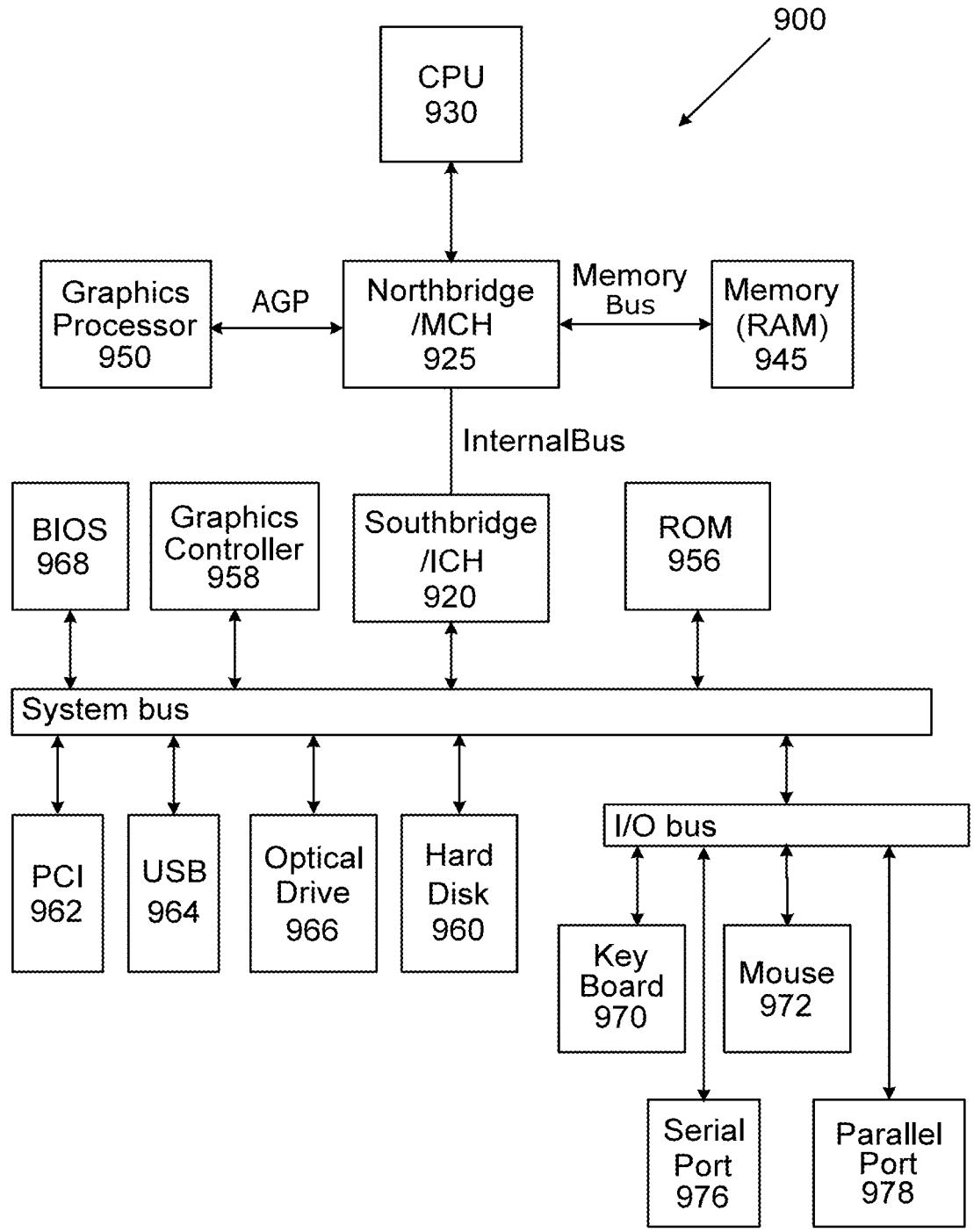
FIG. 9 is a schematic block diagram of a data processing system associated with the data collection unit of the method of the present disclosure.

FIG. 9 shows a schematic diagram of a data processing system, according to certain embodiments, for accumulating the set of transmission coefficients. The data processing system is an example of a computer in which code or instructions implementing the processes of the illustrative embodiments may be located.

In FIG. 9, data processing system 900 employs a hub architecture including a north bridge and memory controller hub (NB/MCH) 925 and a south bridge and input/output (I/O) controller hub (SB/ICH) 920. The central processing unit (CPU) 930 is connected to NB/MCH 925. The NB/MCH 925 also connects to the memory 945 via a memory bus, and connects to the graphics processor 950 via an accelerated graphics port (AGP). The NB/MCH 925 also connects to the SB/ICH 920 via an internal bus (e.g., a unified media interface or a direct media interface). The CPU Processing unit 930 may contain one or more processors and even may be implemented using one or more heterogeneous processor systems.

Figure 10:
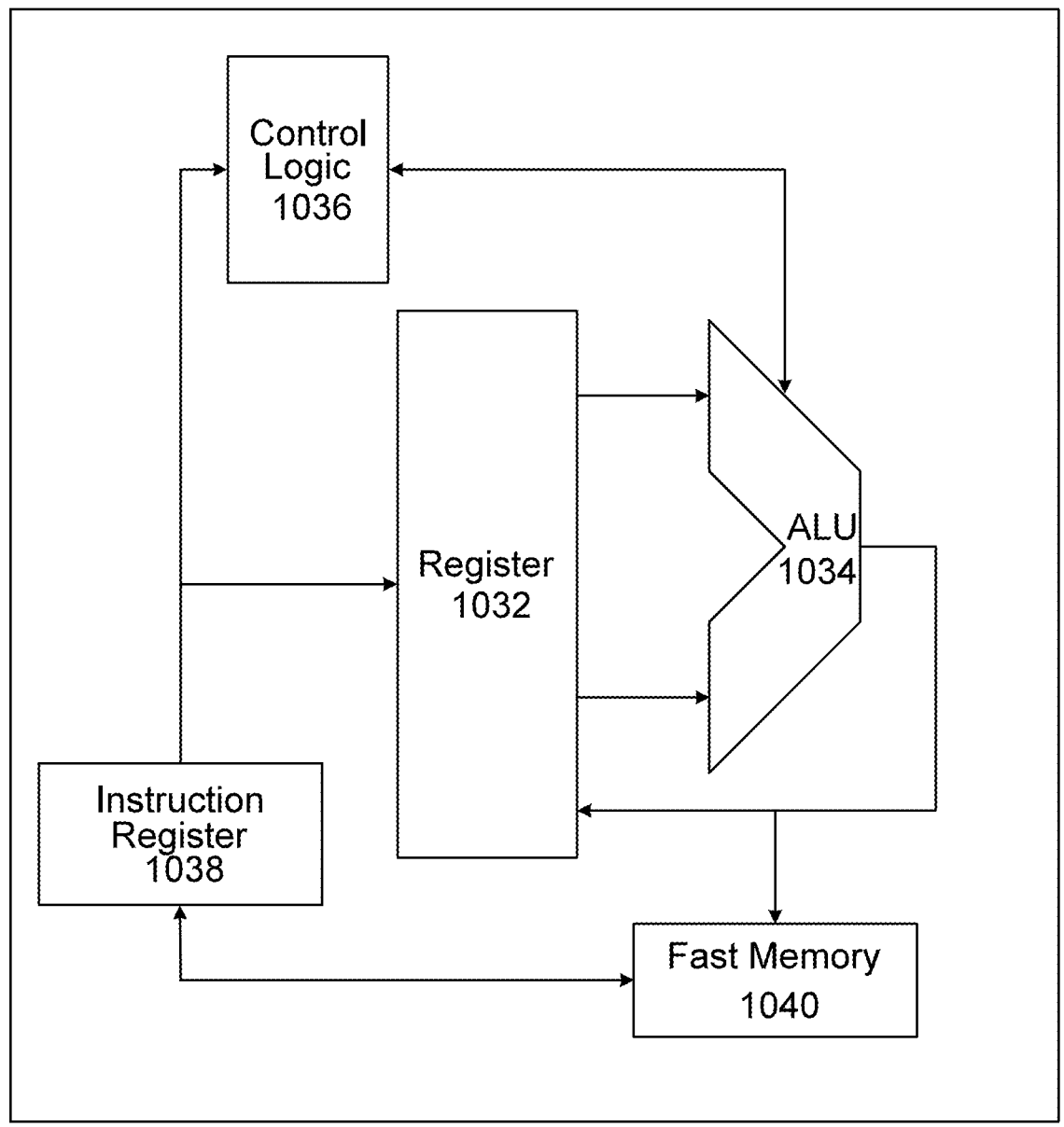
FIG. 10 is a schematic block diagram illustrating one implementation of a central processing unit associated with the average dielectric constant estimating process of the method of the present disclosure.

For example, FIG. 10 shows one implementation of CPU 930. In one implementation, the instruction register 1038 retrieves instructions from the fast memory 1040. At least part of these instructions are fetched from the instruction register 1038 by the control logic 1036 and interpreted according to the instruction set architecture of the CPU 930. Part of the instructions can also be directed to the register 1032. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 1034 that loads values from the register 1032 and performs logical and mathematical operations on the loaded values according to the instructions. The results from these operations can be feedback into the register and/or stored in the fast memory 1040. According to certain implementations, the instruction set architecture of the CPU 930 can use a reduced instruction set architecture, a complex instruction set architecture, a vector processor architecture, a very large instruction word architecture. Furthermore, the CPU 930 can be based on the Von Neuman model or the Harvard model. The CPU 930 can be a digital signal processor, an FPGA, an ASIC, a PLA, a PLD, or a CPLD. Further, the CPU 930 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 9, the data processing system 900 can include that the SB/ICH 920 is coupled through a system bus to an I/O Bus, a read only memory (ROM) 956, universal serial bus (USB) port 964, a flash binary input/output system (BIOS) 968, and a graphics controller 958. PCI/PCIe devices can also be coupled to SB/ICH 920 through a PCI bus 962.

The PCI devices may include, for example, Ethernet adapters, add-in cards, and PC cards for notebook computers. The Hard disk drive 960 and CD-ROM 966 can use, for example, an integrated drive electronics (IDE) or serial advanced technology attachment (SATA) interface. In one implementation the I/O bus can include a super I/O (SIO) device.

Further, the hard disk drive (HDD) 960 and optical drive 966 can also be coupled to the SB/ICH 920 through a system bus. In one implementation, a keyboard 970, a mouse 972, a parallel port 978, and a serial port 976 can be connected to the system bust through the I/O bus. Other peripherals and devices that can be connected to the SB/ICH 920 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 11:
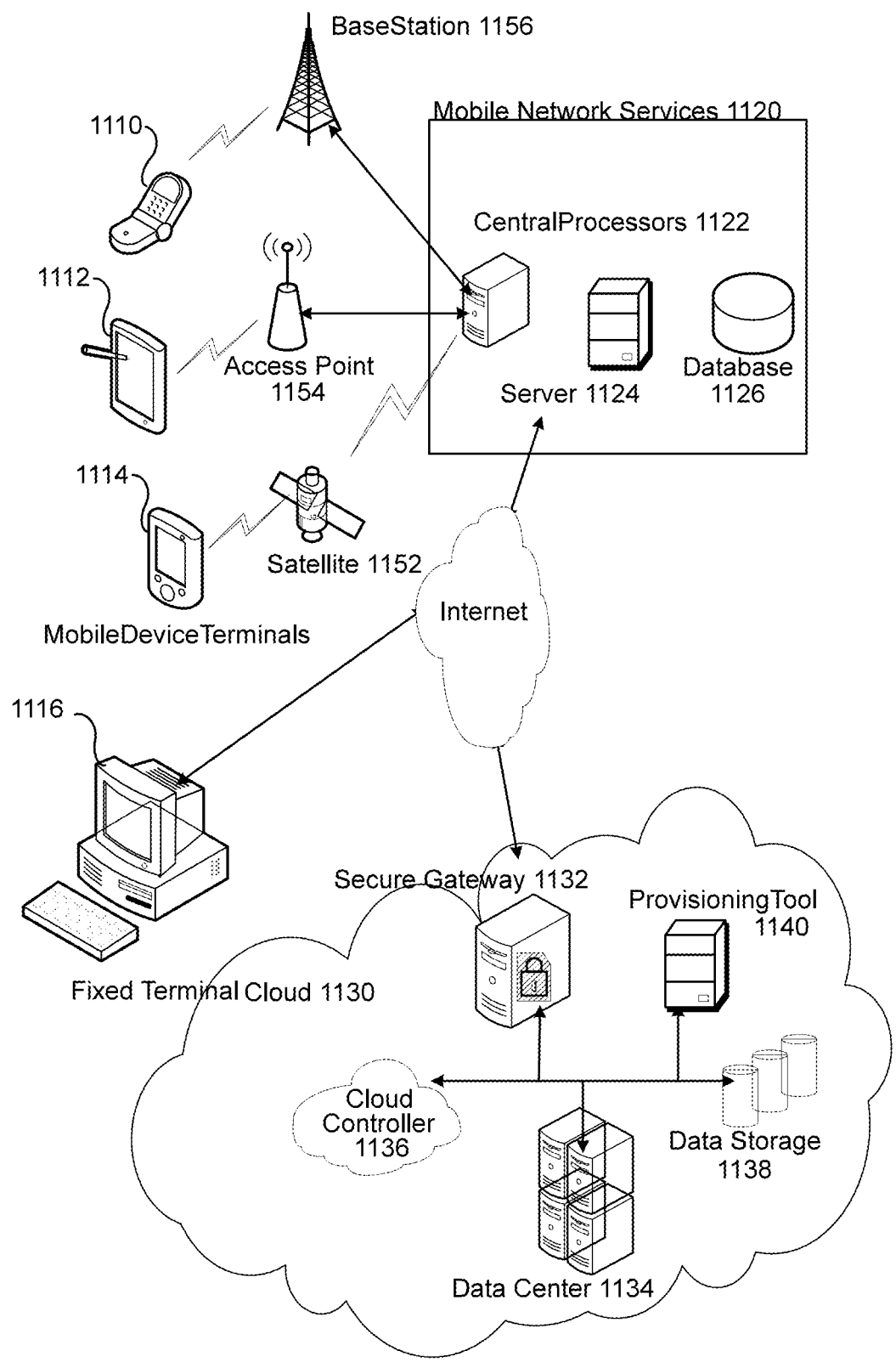
FIG. 11 is a schematic block diagram illustrating the process of utilizing multiple processors distributed across a network for the dielectric constant estimating process.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 11, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Terminology used herein is for the purpose of describing particular embodiments only and is not intended to be limiting of the invention.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

Obviously, numerous modifications and variations of the present invention are possible in light of the above teachings. It is therefore to be understood that within the scope of the appended claims, the invention may be practiced otherwise than as specifically described herein.

The invention claimed is:

1. A system for detecting pulmonary edema and emphysema, comprising:
   a radio frequency (RF) sensor array,
   wherein the RF sensor array comprises a plurality of electrodes and a plurality of ports, wherein a distance between two consecutive ports of the plurality of ports is within a range of 0.20 centimeters (cm)-0.25 cm, wherein the plurality of electrodes comprises an exciting electrode and a set of remaining electrodes, wherein a width of the exciting electrode is within a range of 0.5 cm-0.6 cm, wherein a width of each of the set of remaining electrodes is within a range of 1 cm-3 cm, wherein a length of each of the plurality of electrodes is within a range of 3 cm-5 cm, wherein the RF sensor array comprises 38 electrodes and 37 ports;
   a data collection unit;
   a body area network (BAN);
   a post-processing unit;
   the RF sensor array being fabricated along an outer layer of a flexible substrate, wherein the flexible substrate is perimetrically positioned around a human torso, wherein the RF sensor array measures a set of transmission coefficients;
   the RF sensor array being communicably coupled with the data collection unit through a microcontroller and a RF switch; and
   the data collection unit being communicably coupled with the post-processing unit through the BAN, wherein the BAN wirelessly transfers the set of transmission coefficients to the post-processing unit, wherein the post-processing unit includes circuitry with instructions configured to estimate an average dielectric constant from the set of transmission coefficients.

2. The system for detecting pulmonary edema and emphysema as of claim 1, wherein an operating frequency of the RF sensor array is within a range of 50 Megahertz (MHz)-75 MHz, wherein an input power of the RF sensor is within a range of 0.5 MW-1.5 MW.

3. The system for detecting pulmonary edema and emphysema as of claim 1, wherein a depth of measurement for the RF sensor array is within a range of 10 centimeters (cm)-12 cm.

4. The system for detecting pulmonary edema and emphysema as of claim 1, wherein the flexible substrate is a flexible polyimide sheet, wherein a thickness of the flexible substrate is within a range of 25 micrometers (μm)-75 μm.

5. The system for detecting pulmonary edema and emphysema as of claim 1, wherein a length of the flexible substrate is within a range of 85.0 cm-95.0 cm.

6. The system for detecting pulmonary edema and emphysema as of claim 1, wherein a width of the flexible substrate is within a range of 4.0 cm-5.0 cm.

7. A method of detecting pulmonary edema and emphysema using the system of claim 1, comprising:
   determining a simulated set of transmission coefficients for the plurality of ports to calibrate the RF sensor array positioned around a human chest model,
   wherein the simulated set of transmission coefficients is determined using a high frequency structure simulator (HFSS) module,
   wherein each of the simulated set of transmission coefficients corresponds to a port of the plurality of ports,
   wherein the simulated set of transmission coefficients is determined for a set of varying dielectric constants, a set of varying conductivity values, and a set of varying loss tangent values of the human chest model;
   generating an overdetermined matrix for the simulated set of transmission coefficients at the post-processing unit;

applying a method of least squares to the overdetermined matrix to determine a weight coefficient for each of the plurality of ports;

determining a measured set of transmission coefficients using the RF sensor array, wherein the RF sensor array is perimetrically positioned around a chest with the flexible substrate;

activating the RF switch to transfer the measured set of transmission coefficients to the data collection unit using the microcontroller;

accumulating the measured set of transmission coefficients using the data collection unit;

transferring the set of measured transmission coefficients from the data collection unit to the post-processing unit using the BAN; and estimating an average dielectric constant from the measured set of transmission coefficients as a sum of products of the weight coefficient of each port and the measured transmission coefficient of each port, wherein the measured set of transmission coefficients includes the measured transmission coefficient.

8. A method of detecting pulmonary edema and emphysema using the system of claim 7, wherein a dielectric constant of an inner layer of the human chest model is varied from 1 to 120 as the set of varying dielectric constants.

9. A method of detecting pulmonary edema and emphysema using the system of claim 7, wherein a conductivity of an inner layer of the human chest model is varied from 0.3 siemens/meter (S/m)-0.5 S/m as the set of varying conductivity values.

10. A method of detecting pulmonary edema and emphysema using the system of claim 7, wherein a loss tangent value of an inner layer of the human chest model is varied from 2 to 3 as the set of varying loss tangent values.

11. The method of detecting pulmonary edema and emphysema using the system as of claim 7, wherein determining the measured set of transmission coefficients for the plurality of ports, comprising:

determining a set of preliminary transmission coefficients for a selected port of the plurality of ports, wherein the set of preliminary transmission coefficients is measured with a vector network analyzer (VNA); and averaging the set of preliminary transmission coefficients of the selected port to determine the measured transmission coefficient for the selected port.

12. The method of detecting pulmonary edema and emphysema using the system as of claim 7, wherein the overdetermined matrix comprises 480 rows and 36 columns.

13. The method of detecting pulmonary edema and emphysema using the system as of claim 7, wherein a dielectric assessment kit (DAK) is used to measure the set of varying dielectric constants, the set of varying conductivity values, and the set of varying loss tangent values of applied at an inner layer of the human chest model.

* * * * *